United States Patent
Bernstein

[11] Patent Number: 5,908,256
[45] Date of Patent: Jun. 1, 1999

[54] BOTTLE WITH BUILT-IN TELESCOPING APPLICATOR HEAD AND VALVE THEREIN

[76] Inventor: Melvin Bernstein, 714 Jeffrey Dr., Baldwin, N.Y. 11510

[21] Appl. No.: 08/783,059

[22] Filed: Jan. 14, 1997

Related U.S. Application Data

[63] Continuation-in-part of application No. 08/319,810, Oct. 7, 1994, abandoned.

[51] Int. Cl.⁶ .................................................... A45D 34/00
[52] U.S. Cl. ................................ 401/205; 401/6; 401/23; 401/136; 401/186; 401/270; 401/207
[58] Field of Search .................................. 401/6, 23, 205, 401/270, 277, 186, 136, 207; 222/523, 464.5

[56] References Cited

U.S. PATENT DOCUMENTS

| | | |
|---|---|---|
| 193,024 | 7/1877 | Newton ..................................... 401/205 |
| 457,826 | 8/1891 | Meeker . |
| 513,071 | 1/1894 | Baldwin .................................. 401/277 |
| 960,008 | 5/1910 | Evans et al. . |
| 979,377 | 12/1910 | Campbell . |
| 986,926 | 3/1911 | Mahler . |
| 1,047,852 | 12/1912 | Strickland . |
| 1,473,925 | 11/1923 | Dryer . |
| 1,797,676 | 3/1931 | Baker . |
| 1,960,738 | 5/1934 | Giezentanner . |
| 2,040,625 | 5/1936 | Myers . |
| 2,119,646 | 6/1938 | Pidel . |
| 2,609,558 | 9/1952 | Johnson ............................. 401/270 X |
| 2,718,023 | 9/1955 | Douglass, Jr. .......................... 401/186 |
| 3,106,741 | 10/1963 | Stoner . |
| 3,133,310 | 5/1964 | Yorker et al. . |
| 3,261,515 | 7/1966 | Luedtke . |
| 3,372,846 | 3/1968 | Berkus . |
| 4,135,274 | 1/1979 | Freeman . |
| 4,461,406 | 7/1984 | Vannucci . |
| 4,553,871 | 11/1985 | Niles . |
| 4,726,491 | 2/1988 | Moon . |
| 4,961,661 | 10/1990 | Sutton et al. . |
| 5,547,303 | 8/1996 | Pyrozyk .............................. 401/277 X |

FOREIGN PATENT DOCUMENTS

| | | |
|---|---|---|
| 104197 | 4/1966 | Denmark . |
| 1420454 | 11/1965 | France . |

*Primary Examiner*—Steven A. Bratlie
*Attorney, Agent, or Firm*—Frishauf, Holtz, Goodman, Langer & Chick

[57] ABSTRACT

A combined actuator and bottle for storing a fluid and applying the fluid, includes a container having an opening; an elongated tube having a longitudinal axis, the tube being located in the opening, and the tube being slidable along the longitudinal axis relative to the container and being sealed against the container so that an intake end of the tube is located within the container and an outlet end of the tube is located outside the container; the tube having a duct extending in the direction of the longitudinal axis of the tube, the duct forming a fluid connection between the outlet end of the tube and the intake end that is situated within the container; an applicator head mounted at the outlet end of the tube and having an applicator member receiving the fluid from the outlet end of the tube and supplying the fluid to a dispensing opening thereof having an axis which is substantially transverse to a sliding direction of the tube; and a valve assembly mounted in the applicator head, the valve assembly including a hollow area in the applicator head which slidably receives the outlet end of the tube therein, and a flange at the outlet end of the tube which forms a seal with walls of the applicator head in the hollow area for one of selectively (a) blocking flow of the fluid to the dispensing opening, and (b) permitting flow of the fluid to the dispensing opening.

33 Claims, 13 Drawing Sheets

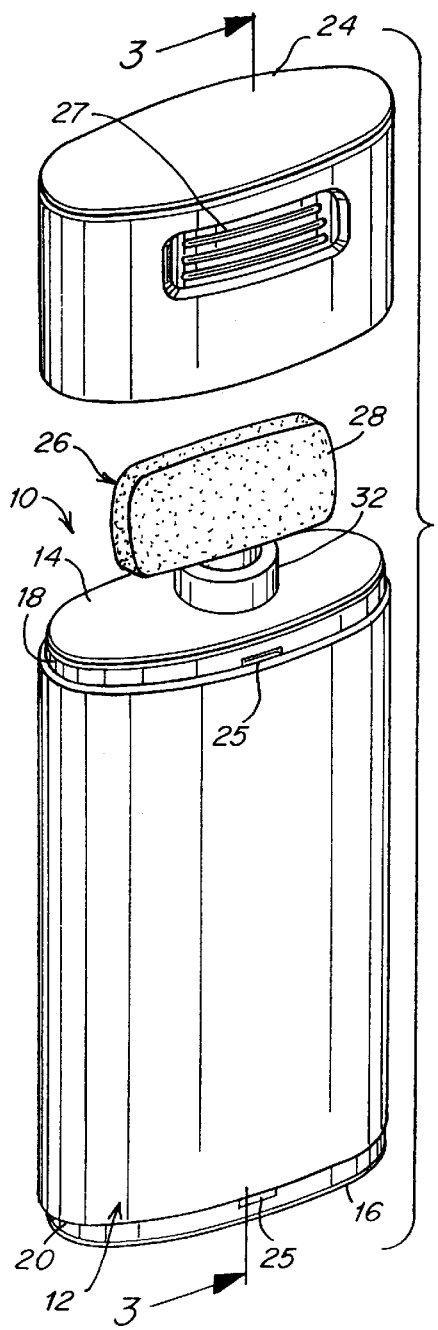
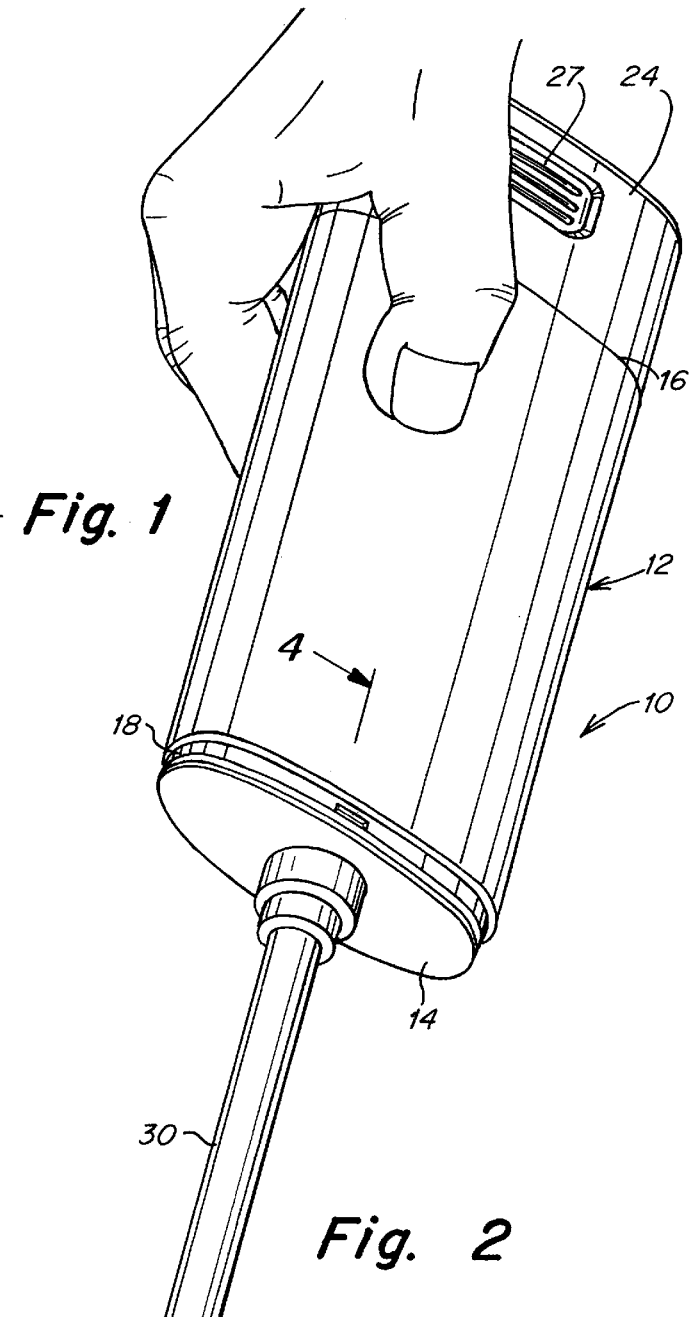
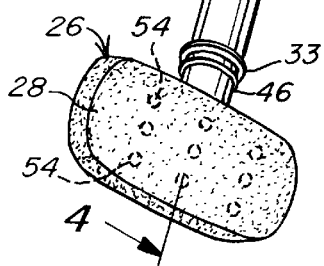
Fig. 1
Fig. 2

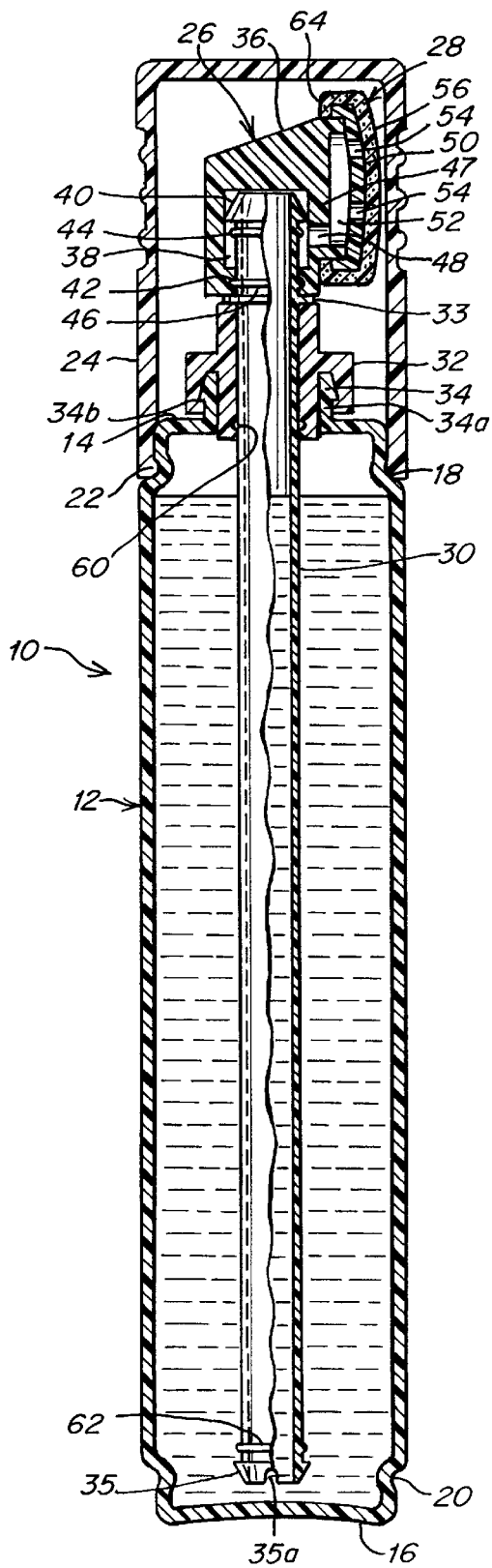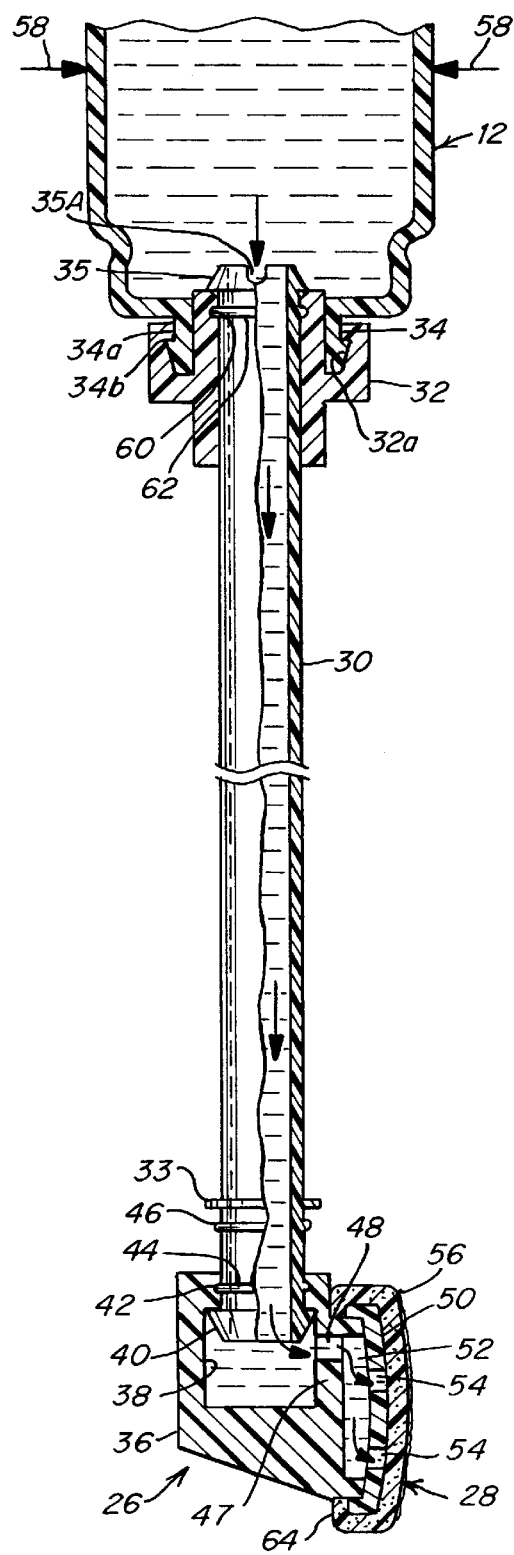
Fig. 3
Fig. 4

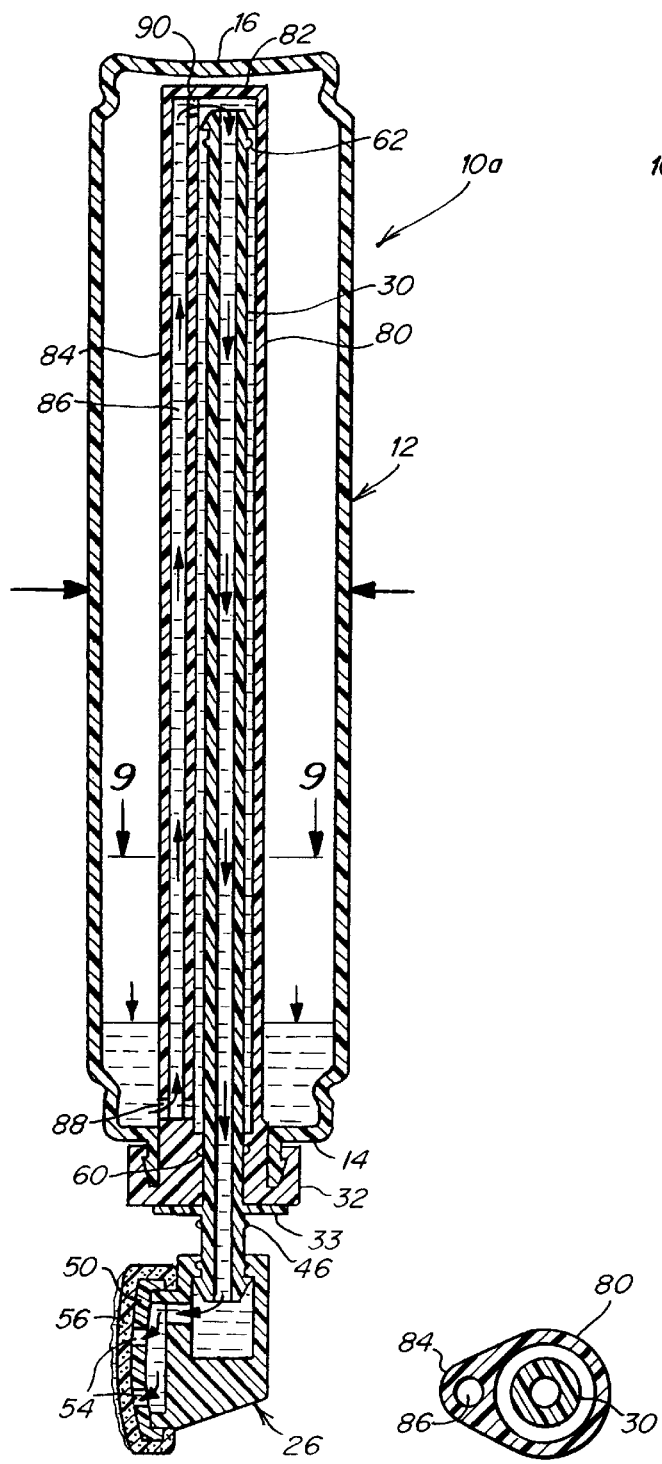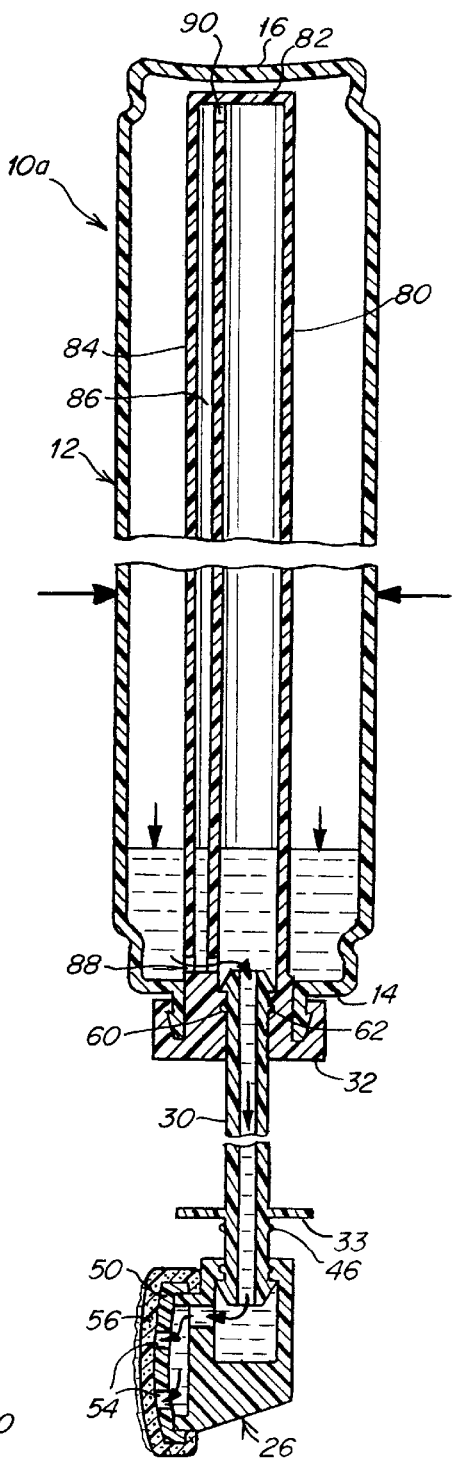
Fig. 8   Fig. 9   Fig. 10

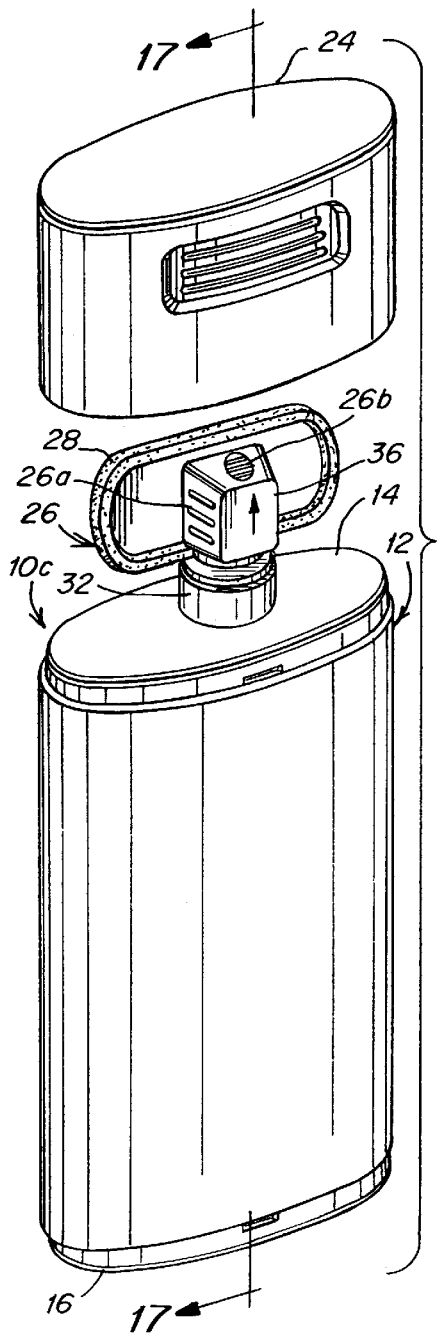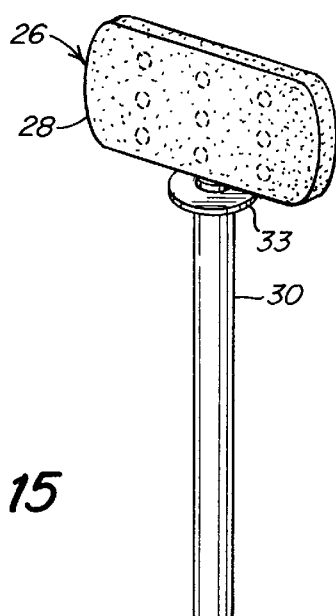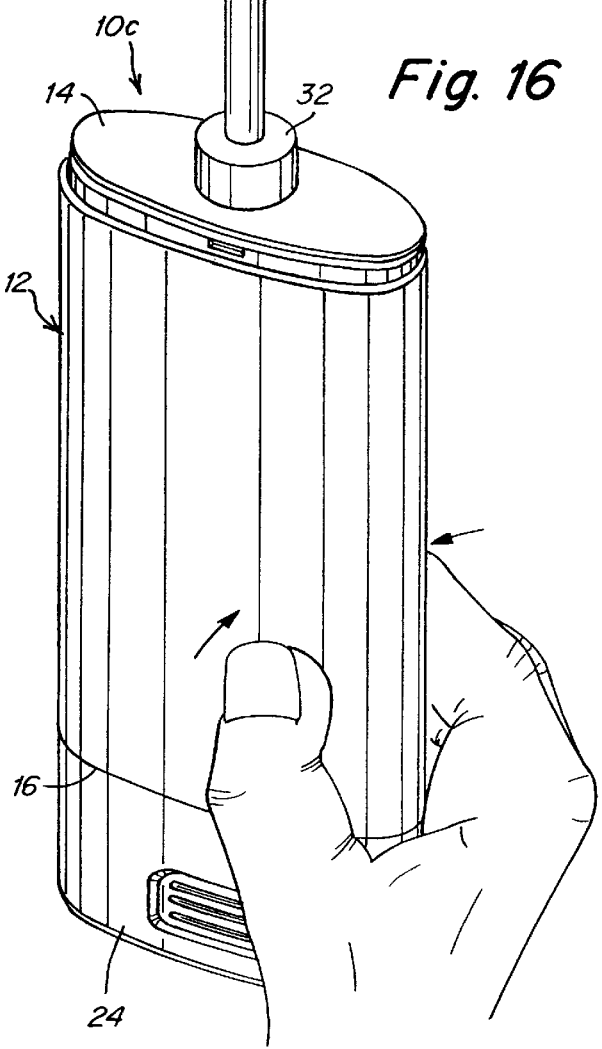
Fig. 15
Fig. 16

BOTTLE WITH BUILT-IN TELESCOPING APPLICATOR HEAD AND VALVE THEREIN

REFERENCE TO RELATED APPLICATION

The present application is a continuation-in-part of U.S. patent application Ser. No. 08/319,810, filed Oct. 7, 1994 now abandoned, by Melvin Bernstein et al, and entitled Bottle With Built-In Telescoping Applicator Head and Spout for Applying Fluid to a Body, the entire contents of which are incorporated herein by reference.

FIELD OF THE INVENTION

This invention relates to a bottle which contains a fluid, such as a lotion (i.e., a suntan lotion, skin lotion), medication, cleanser or the like, the bottle having a built-in applicator and spout for applying the fluid to various body parts, especially inaccessible body parts such as the back of a person, to external wall surfaces and the like. For example, the present invention is particularly useful to people with arthritis who cannot reach various parts of their body, ceilings in shower stalls, etc. The present invention is helpful for such people to apply such fluids, lotions, medications or the like to such difficult-to-reach body parts or wall surfaces.

Hereinafter, the contents of the bottle will be referred to simply as a fluid, for ease of description.

BACKGROUND OF THE INVENTION

Various containers, spouts, pullout spouts and applicator systems, such as those described below, are known.

Containers having pullout spouts for pouring a liquid are known, for example, from U.S. Pat. Nos. 1,473,295 (Dryer), 1,797,676 (Baker), 2,040,625 (Myers), 3,372,846 (Berkus), 4,461,406 (Vannucci), 4,726,491 (Moon). In such case, the pullout spout is generally located within an opening of, and sealingly connected with, the container. The pullout spout is movable like a telescope between a fully retracted position where its outlet is within the opening of the container and a fully protruded position. In many instances, the container opening as well as the pullout spout are provided with threads for threadedly connecting a sealing cap. When attached, the sealing cap engages the pullout spout and the thread of the opening, to close the container opening to prevent leakage of the contents of the container. Alternatively, the threads can be provided on the end of the pullout spout.

However, such devices merely dispense the liquid out from a relatively large opening in order to pour the liquid. There is no means for dispensing the liquid in a slow, uniform flow, for example, for scrubbing an external surface or a body part.

Although applicator heads are known which are fixed to an opening of a bottle or other container, for example, as disclosed in U.S. Pat. Nos. 3,261,515 (Luedtke) and 4,961,661 (Sutton et al), valves for preventing liquid flow are formed in the bottle opening and not in the applicator heads. For example, in U.S. Pat. No. 4,961,661 to Sutton et al, a plug connected with the inner wall of the tube that supports the applicator head, is provided within the duct of the tube, which plug closes the bore when the tube is tightly screwed onto the cap. A similar arrangement is provided in U.S. Pat. No. 3,261,515 to Luedtke. However, it is desirable to provide the valve in the applicator head mounted to a telescoping tube for better control, which is not shown by these references.

Applicator heads, such as sponges and the like, are known to be secured to the end of a telescoping tube. See, for example, U.S. Pat. Nos. 1,047,852 (Strickland), 2,119,646 (Pidel), 3,106,741 (Stoner) and 4,135,274 (Freeman), as well as Danish Patent No. 104,197. However, no valves are provided in the applicator heads to prevent fluid flow when the applicator heads are extended.

SUMMARY OF THE INVENTION

Accordingly, it is an object of the present invention to provide an improved bottle that overcomes the aforementioned problems with the prior art.

It is another object of the present invention to provide an improved bottle having a telescoping tube which is especially useful to apply fluid from the bottle to difficult-to-reach areas.

It is still another object of the present invention to provide such a bottle in which the shut-off valve for the fluid is provided at the outer end of the telescoping tube.

It is yet another object of the present invention to provide a bottle which is easy to use, which is relatively easy to manufacture, and which can be easily closed in a leak-proof manner when desired.

In accordance with the present invention, a combined actuator and bottle for storing a fluid and for applying the fluid, includes a container having an opening; an elongated tube having a longitudinal axis, the tube being located in the opening, and the tube being slidable along the longitudinal axis relative to the container and being sealed against the container so that an intake end of the tube is located within the container and an outlet end of the tube is located outside the container; the tube having a duct extending at least partially in the direction of the longitudinal axis of the tube, the duct forming a fluid connection between the outlet end of the tube and the intake end that is situated within the container; an applicator head mounted at the outlet end of the tube and having an applicator member for receiving the fluid from the outlet end; and a valve assembly mounted in the applicator head for one of selectively (a) blocking flow of the fluid to the applicator member, and (b) permitting flow of the fluid to the applicator member.

The applicator head includes a dispensing opening, preferably having an axis which is substantially transverse to a sliding direction of the tube in the hollow area. The valve assembly includes a hollow area in the applicator head which slidably receives the outlet end of the tube therein, and the outlet end of the tube which forms a seal with walls of the applicator head in the hollow area for one of selectively (a) blocking flow of the fluid to the dispensing opening, and (b) permitting flow of the fluid to the dispensing opening. Specifically, the outlet end of the tube includes an annular flange that forms a seal with the walls of the applicator head.

A locking assembly can releasably lock the outlet end of the tube in a first position in the hollow area to block flow of the fluid to the dispensing opening, and a second position in the hollow area to permit flow of the fluid to the dispensing opening. Preferably, the locking assembly includes an annular groove in an opening wall of the applicator head, a first bead on the tube which engages with the annular groove in the first position and a second bead on the tube which engages with the annular groove in the second position.

The applicator head includes a main body having the hollow area, a manifold mounted to the main body, and an absorbent pad mounted on the manifold, the manifold being in fluid communication with the dispensing opening for dispensing fluid to the absorbent pad.

In an alternative embodiment, the absorbent pad and manifold are pivotally mounted to the main body such that the fluid can be dispensed through the manifold and absorbent pad when the manifold and absorbent pad are in a closed position, and can be dispensed directly through the dispensing opening when the manifold and absorbent pad are pivoted to an open position. In this embodiment, the main body further includes a nozzle in communication with the dispensing opening, and the manifold includes a boss having an opening for receiving the nozzle when the manifold and absorbent pad are pivoted to the closed position.

The intake end of the tube includes a bead therearound, and the container at the opening includes an annular groove for receiving the bead to releasably hold the tube in an extended position. A stop is positioned around the tube near the outlet end thereof for limiting retraction of the tube into the container.

The container is made of a resilient and deformable material that permits squeezing thereof. Also, the actuator member is releasably mounted to the actuator head. Preferably, the actuator member is an absorbent pad, although it can be any other suitable member, such as brushes mounted to the actuator head.

In accordance with another aspect of the present invention, a combined actuator and bottle for storing a fluid and for applying the fluid, includes a container having an opening; an elongated tube having a longitudinal axis, the tube being located in the opening, and the tube being slidable along the longitudinal axis relative to the container and being sealed against the container so that an intake end of the tube is located within the container and an outlet end of the tube is located outside the container; the tube having a duct extending at least partially in the direction of the longitudinal axis of the tube, the duct forming a fluid connection between the outlet end of the tube and the intake end that is situated within the container; an applicator head mounted at the outlet end of the tube and having an applicator member for receiving the fluid from the outlet end; a valve assembly mounted in the applicator head for one of selectively (a) blocking flow of the fluid to the applicator member, and (b) permitting flow of the fluid to the applicator member; and a tube member in the container in surrounding and spaced relation to the tube and which provides a path of travel of the fluid from the container to the tube.

In one embodiment, the tube member includes a transverse extension along substantially the entire length thereof, the transverse extension including a longitudinal opening parallel to the tube, and the longitudinal opening is in fluid communication with the fluid in the container adjacent a top end of the container through a first transverse opening in the extension, and is in fluid communication with the tube adjacent a bottom of the container through a second transverse opening in the extension. In this embodiment, the fluid in the container is in fluid communication with the tube through the first transverse opening when the tube is in a fully extended position.

In another embodiment, the tube is in fluid communication with the fluid in the container adjacent a top end of the container through a first transverse opening in the tube member and an annular space between the tube and the tube member when the container is turned upside down, and is in fluid communication with the fluid in the container adjacent a bottom of the container through a second transverse opening in the tube member when the container is upright.

The above and other objects, features and advantages of the present invention will become readily apparent from the following detailed description which is to be read in connection with the accompanying drawings.

BRIEF DESCRIPTION OF THE DRAWINGS

FIG. 1 is a perspective view of a bottle for applying fluid according to a first embodiment of the present invention, showing the telescoping tube in a retracted position;

FIG. 2 is a perspective view of the bottle of FIG. 1 with the tube in an extended position, ready for use;

FIG. 3 is a longitudinal sectional view taken along line 3—3 in FIG. 1 of the bottle with the telescoping tube in the retracted position and with the cover closed;

FIG. 4 is a longitudinal sectional view taken along line 4—4 in FIG. 2 of the bottle with the telescoping tube in the extended position and with the cover mounted to the bottom of the container;

FIG. 8 is a longitudinal sectional view of a bottle according to a second embodiment of the present invention, with the tube fully retracted and the valve assembly open;

FIG. 9 is a cross-sectional view taken along line 9—9 in FIG. 8;

FIG. 10 is a longitudinal sectional view of the bottle of FIG. 8, with the tube fully extended and the valve assembly open;

FIG. 15 is a perspective view of a bottle for applying fluid according to a fourth embodiment of the present invention, showing the telescoping tube in a retracted position;

FIG. 16 is a perspective view of the bottle of FIG. 15 with the tube in an extended position, ready for use;

DETAILED DESCRIPTION

Figure 5:
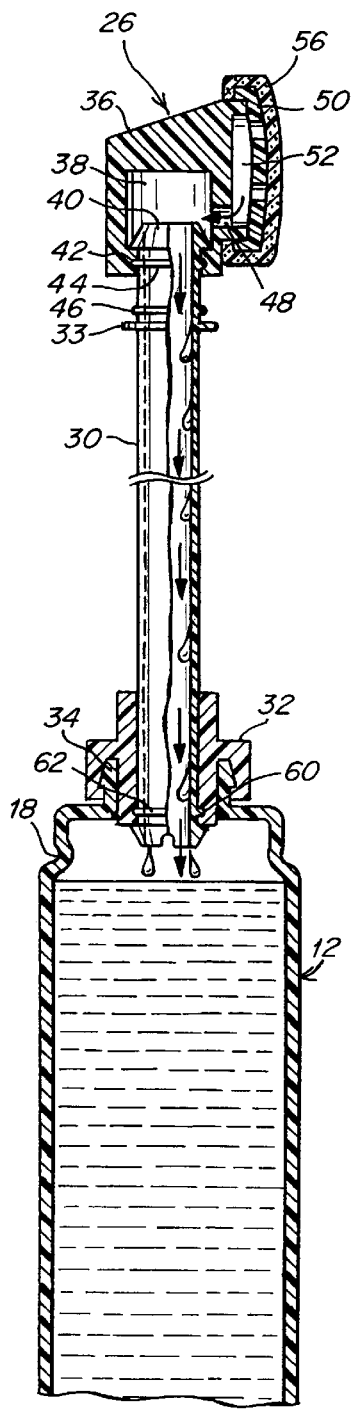
FIG. 5 is a longitudinal sectional view similar to FIG. 4, with the bottle placed upright to allow fluid to drain from the applicator head and tube back into the bottle.

Referring to the drawings in detail, and initially to FIGS. 1–7 thereof, a combined applicator and bottle 10 according to a first embodiment of the present invention includes a hand holdable container 12, preferably with an elliptical or oval cross-section, and having a top end 14 and a bottom 16. Container 12 is preferably made from a resilient or flexible squeezable material, such as plastic, and is filled with fluid which is to be applied to a human body or to be applied to an external wall surface such as for scrubbing tile or the like. Although container 12 is shown as having an oval cross-section, container 12 may have any other suitable shape, such as round or any other desired cross-section. Top end 14 and bottom 16 of container 12 are each recessed and form grooves 18 and 20, respectively, which are arranged to receive a respective engaging shoulder 22 of a cap 24 in order to carry cap 24 thereon, as shown best in FIGS. 3 and 4. Preferably, snap detents 25 are provided in grooves 18 and 20 for engaging with corresponding projections in cap 24 in order to aid in securing cap 24 thereon. In addition, cap 24 includes finger grips 27.

An applicator head 26, with an applicator member 28, such as a pad for dispensing and applying fluid, is supported at the top end 14 of container 12 by a telescoping hollow tube 30. Telescoping tube 30 is slidable and is sealingly received in a sleeve 32 fixed to the neck 34 of container 12, and provides fluid communication between applicator head 26 and the inner space of container 12.

Sleeve 32 is preferably a molded part having a recess 32a therein (see FIG. 4). In this regard, neck 34 has an upwardly extending annular portion 34a with a hook-like member 34b thereon which snappingly engages into the mating recess 32a of sleeve 32. The upper portion 34a of container 12 is thereby resiliently engaged with neck 32, which is preferably made of a resilient material which snaps over hook-like member 34b of container 12. In this manner, after assembly, sleeve 32 is locked in position and cannot be inadvertently removed.

Tube 30 is restrained within sleeve 32 by a stop washer 33 near its outlet end and a flange 35 at its intake end, thereby limiting sliding movement of tube 30. Thus, tube 30 cannot inadvertently be pulled out of sleeve 32 of container 12. In addition, flange 35 provides a seal between tube 30 and container 12 when tube 30 is in its fully extended position shown in FIG. 4. As shown best in FIG. 4, flange 35 is provided with a slot 35a to provide maximum drain of fluid from container 12 when there is a low product level and container 12 is turned upside down.

Applicator head 26 is movable with tube 30, so that it can be pulled outwardly with tube 30 into the extended position, as illustrated in FIGS. 2 and 4, and can thereafter be pushed into the retracted position illustrated in FIGS. 1 and 3. Cap 24 may be engaged on bottom grooves 20 of container 12 during use (see FIG. 2), thereby increasing the overall length of the entire bottle 10 when desired, especially when applicator head 26 is in the extended position, thereby facilitating application of the fluid to the body or wall surfaces, and also facilitating handling of the bottle during use.

The movable (extendable) applicator head 26 comprises a body 36 with a generally cylindrical hollow area 38 that slidably receives the output end of tube 30. In this regard, the outlet end of tube 30 includes a frusto-conical shaped flange 40 having outer dimensions similar to those of the inner dimensions of hollow area 38 but capable of sliding therein between the positions shown in FIGS. 3 and 4. Further, applicator head 26 includes an annular groove 42 at the entrance to hollow area 38, and tube 30 includes two axially spaced annular beads 44 and 46 at the outlet end thereof.

When applicator head 26 is pushed down on tube 30, as shown in FIG. 3, lower bead 46 engages within groove 42 to releasably hold applicator head 26 in this position. In such position, in view of the similar dimensions of the outer dimensions of frusto-conical shaped flange 40 to those of the inner dimensions of hollow area 38, a valve seal is provided which prevents flow of fluid out from applicator head 26. Alternatively, and/or in addition to this valve seal, the upper edge of flange 40 can be dimensioned to abut against the upper surface of the wall defining hollow area 38 to provide a valve seal thereat. Thus, a push/pull valve arrangement is provided.

When applicator head 26 is pulled up from tube 30, as shown in FIG. 4, upper bead 44 engages within groove 42 to releasably hold applicator head 26 in this position. In such position, as will be explained hereinafter, fluid is permitted to flow out from applicator head 26, that is, the valve therein is open.

Applicator head 26 includes a dispensing opening 48 in a side wall 47 thereof, having an axis orthogonal to that of the axis of tube 30. Thus, when applicator head 26 is in the position shown in FIG. 4, fluid can flow from the outlet end of tube 30 to opening 48. However, when applicator head 26 is in the position shown in FIG. 3, the fluid from tube 30 is blocked by flange 40, thereby preventing its flow to dispensing opening 48.

Applicator head 26 further includes an apertured, slightly arcuate manifold plate 50 which is secured in spaced relation to side wall 47 so as to form a chamber 52 in communication with dispensing opening 48. Plate 50 includes a plurality of apertures 54 therein and functions as a distribution manifold for the fluid.

Applicator member 28 includes a pad 56 which is made of fabric, foam or any other material that is permeable to the fluid is removably mounted to plate 50. As shown in FIGS. 3 and 4, the permeable, resilient pad 56 has a lip or surround portion 64 which extends over the rear end of the body part of applicator head 26. Since pad 56 is preferably made of a resilient material it remains engaged on the body part of applicator head 26. However, pad 56 is easily removable by stretching it and pulling it off of the body part, as will be explained hereinafter in relation to the other embodiments of the invention, so as to replace it by engaging a new pad 56 over applicator head 26. Pad 56 can be used as a scrubbing pad for bath tubs, shower bases, etc.

Fluid can be dispensed via dispensing opening 48 when cap 24 is removed and when applicator head 26 is extended from tube 30, as shown in FIG. 4. Preferably, this would occur when tube 30 is extended, although fluid can be applied even when tube 30 is in its retracted position, as long as applicator head 26 is extended relative to tube 30 and bottle 10 is held upright. However, it is preferable to dispense the fluid when bottle 10 is held in the upside-down-position, and when bottle 10 is squeezed in the direction of arrows 58, as is shown in FIG. 4, although the present invention would also be operative when the bottle is held upright.

It will be appreciated that there is a limitation on the use of bottle 10 according to the embodiment of FIGS. 1–7. Specifically, when bottle 10 is turned upside down, and with tube 30 fully retracted within container 12, the intake end of tube 30 will be above the fluid level, so that no dispensing can take place. Therefore, when bottle 10 is turned upside down, it can only be used when tube 30 is in the extended position.

However, when applicator head 26 is pushed down on tube 30, as shown in FIG. 3, regardless of whether tube 30 is extended or retracted, dispensing opening 48 is disabled so that there is no fluid communication between inner space of container 12 and dispensing opening 48.

In order to prevent leakage between tube 30 and sleeve 32, sleeve 32 preferably comprises a sealing member (not shown) which is preferably a resilient O-ring made, for example, of rubber, plastic or the like, fitted in an annular groove provided within sleeve 32. It is also possible to form the sealing member in one part with sleeve 32, for example, by forming an annular lip (not shown) at the inner end of sleeve 32, which lip is resilient and wipes against the outer surface of tube 30 when it is pulled out to its extended position.

A detent assembly is provided by an annular recess, such as at least one annular groove 60, on the inner surface of sleeve 32 and by an annular bead 62 provided on the intake end of tube 30. Annular beads 44, 46 and 62 are preferably resilient so that tube 30 can be released from a detention position with a given axial force which is not so great as to make operation difficult by physically infirm persons. Beads 44, 46 and 62 are each preferably formed integrally with tube 30 as annular bulges on the outer circumferential surface of tube 30.

Thus, with the present invention, applicator head 26 is formed at the outlet end of telescoping tube 30 and has a valve assembly formed therein by means of the slidable arrangement of applicator head 26 on flange 40 at the outlet end of tube 30.

After use of bottle 10 has been completed, bottle 10 is preferably turned upright, as shown in FIG. 5. In this position, fluid flows from chamber 52, back through dispensing opening 48, into hollow area 38 and down tube 30 into container 12. Thereafter, downward pressure is applied to applicator head 26 in the direction of arrow 66 in FIG. 6. Because of the engagement of bead 44 in groove 42, and because the resistance force of bead 62 in groove 60 is preferably less than that of bead 44 in groove 42, bead 62 escapes from groove 60, and tube 30 is pushed back into container 12, to the position shown in FIG. 6, until stop washer 33 abuts against the upper end of sleeve 32. It will be appreciated that, in this position, the valve assembly as part of applicator head 26 is still open. This permits air pressure to flow out of applicator head 26, as shown by arrows 67. Then, upon continued pushing on applicator head 26 in the direction of arrow 68 in FIG. 7, bead 44 escapes groove 42, and applicator head 26 is pushed down on tube 30, thereby closing the valve arrangement, and blocking any fluid to dispensing opening 48. Accordingly, bead 46 enters groove 42 to releasably lock applicator head 26 in this position.

Referring now to FIGS. 8–12, a bottle 10a according to a second embodiment of the present invention will now be described, in which elements corresponding to those in the first embodiment of FIGS. 1–7 are identified by the same reference numerals, and a detailed description of the common elements will be omitted for the sake of brevity.

As shown therein, an outer fixed tubular member 80 is provided in surrounding relation to slidable tube 30, and is closed at its end adjacent the intake end of tube 30 (upper end in FIGS. 8 and 10) by a wall 82 in spaced relation to the intake end of tube 30. Tubular member 80 is integrally provided with a transverse extension 84 which extends the length thereof and has a longitudinal opening 86 therein. An upper transverse opening 88 (lower end in FIGS. 8 and 10) provides communication between one end of longitudinal opening 86 and the fluid in container 12. A lower transverse opening 90 at the opposite end of container 12 provides communication between the opposite end of longitudinal opening 86 and tube 30.

With this arrangement, and with tube 30 in the retracted position, when container 12 is turned upside down and squeezed, internal pressure forces fluid from container 12, through transverse opening 88, up longitudinal opening 86, through transverse opening 90 and down tube 30 to applicator head 26. This differs from the first embodiment of FIGS. 1–7 which was not operational in this position.

On the other hand, with tube 30 in the fully extended position, when container 12 is turned upside down and squeezed, longitudinal opening 86 is no longer required. In such case, internal pressure forces fluid from container 12, through transverse opening 88 and down tube 30 to applicator head 26.

Figure 11:
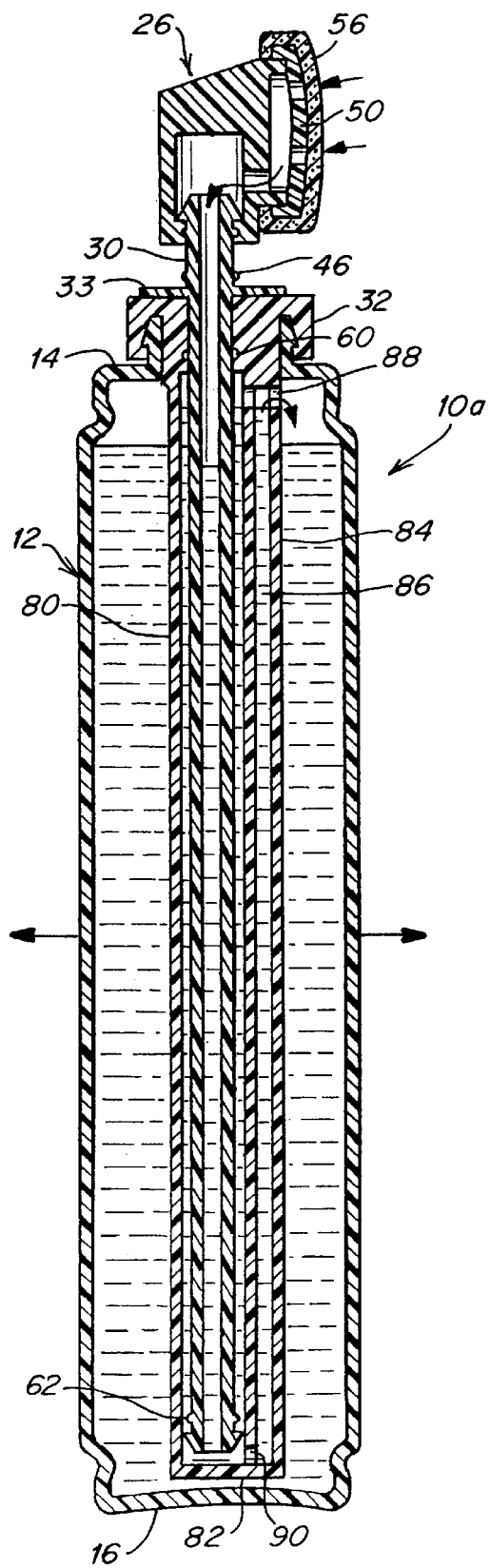
FIG. 11 is a longitudinal sectional view of the bottle of FIG. 8, with the bottle turned upright.
Figure 12:
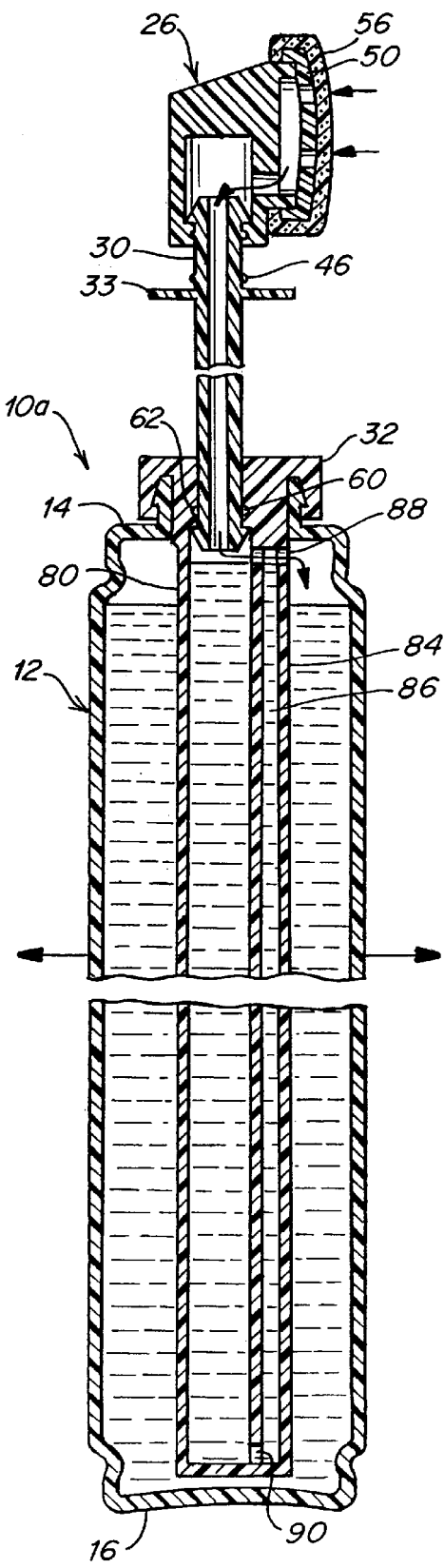
FIG. 12 is a longitudinal sectional view of the bottle of FIG. 10, with the bottle turned upright.

After the dispensing operation has been completed, bottle 10a is turned upright. In such case, the sides of container 12 return to their normal position as a result of the memory in the plastic material of container 12. This creates a negative pressure that sucks the fluid back down from applicator head 26, thereby taking in air to replace the dispensed fluid. Bottle 10a is then ready to close or to turn upside-down again in order to dispense more fluid. This can occur in the retracted position of tube 30, as shown in FIG. 11 or the extended position of tube 30, as shown in FIG. 12.

Figures 13, 14:
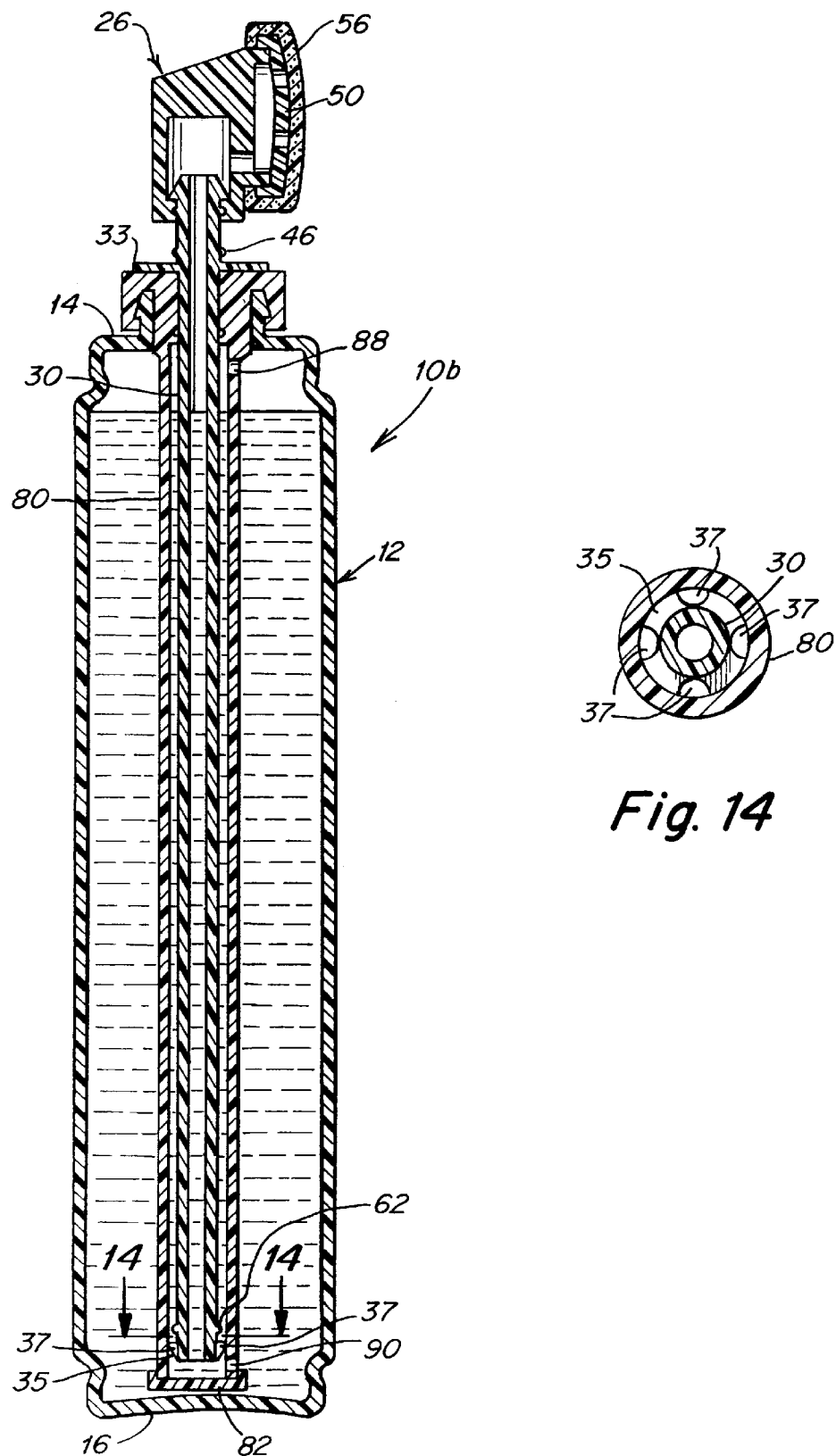
FIG. 13 is a longitudinal sectional view of a bottle according to a third embodiment of the present invention.
FIG. 14 is a cross-sectional view taken along line 14–14 in FIG. 13.

Referring now to FIGS. 13 and 14, a bottle 10b according to a second embodiment of the present invention will now be described, in which elements corresponding to those in bottle 10a according to the second embodiment of FIGS. 8–12 are identified by the same reference numerals, and a detailed description of the common elements will be omitted for the sake of brevity.

Bottle 10b differs from bottle 10a in that flange 35 is provided with passages 37 therethrough. In this case, transverse extension 84 having longitudinal opening 86 therein as in bottle 10a are eliminated. Instead, transverse openings 88 and 90 are provided directly in tubular member 80.

When bottle 10b is held upright, fluid enters through opening 90 into tube 30. On the other hand, when bottle 10b is held upside down, fluid enters through opening 88 and travels in the annular space between tube 30 and tubular member 80, where it then enters tube 30. Thus, bottle 10b can be used in an upright or upside down orientation.

The advantage of bottle 10b is that it is simpler in construction than bottle 10a of FIGS. 8–12.

Referring now to FIGS. 15–24, a bottle 10c according to a fourth embodiment of the present invention will now be described, in which elements corresponding to those in bottles 10, 10a and 10b according to the first through third embodiments are identified by the same reference numerals, and a detailed description of the common elements will be omitted for the sake of brevity.

In this embodiment, tube 30 is surrounded by a surrounding tube member 80 without the aforementioned openings 88 and 90. Further, flange 35 is provided with passages 37 therethrough. Fluid passages 37 thereby provide a pressure relief when tube 30 is pushed down or pulled up.

Figures 17, 18, 19:
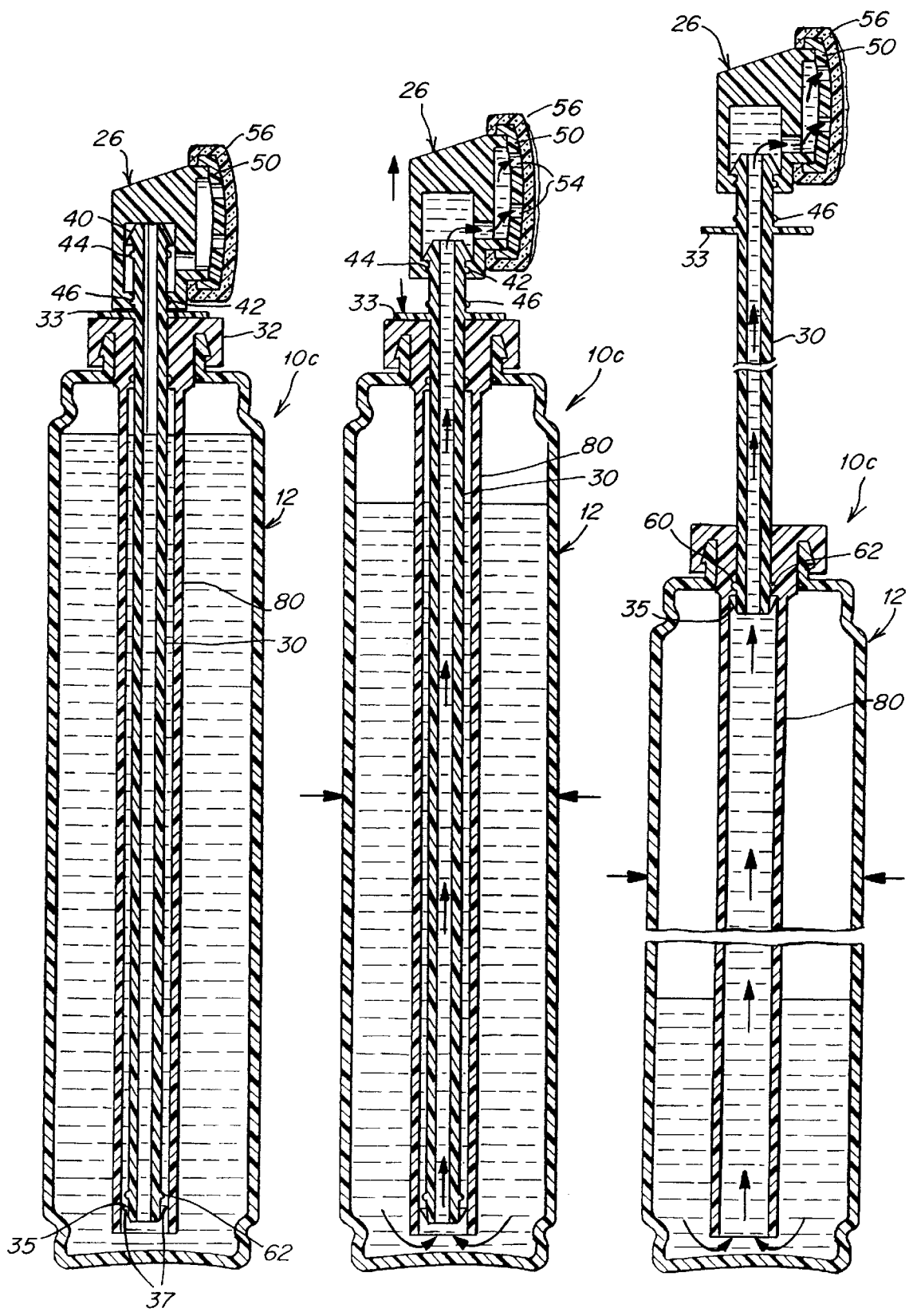
FIG. 17 is a longitudinal sectional view taken along line 17—17 in FIG. 15 of the bottle with the telescoping tube in the retracted position and with the valve assembly in the applicator head closed.
FIG. 18 is a longitudinal sectional view similar to FIG. 17, with the telescoping tube in the retracted position and with the valve assembly in the applicator head open.
FIG. 19 is a longitudinal sectional view similar to FIG. 17, with the telescoping tube in the extended position and with the valve assembly in the applicator head open.

Further, applicator head 26 is constructed slightly differently. In the first place, applicator head 26 is provided with finger grips 26a for pulling applicator head 26 up and an upper thumb grip 26b for pushing applicator head 26 down. Further, stop washer 33 is made of a larger diameter. Thus, while holding down stop washer 33 on sleeve 32, applicator head 26 can be gripped and pulled up until bead 44 engages within groove 42, thus opening up the valve assembly, as shown in FIG. 18. Thereafter, while holding sleeve 32, and continuing to pull up on applicator head 26, tube 30 is retracted from container 12, as shown in FIG. 19.

Bottle 10c according to the fourth embodiment is particularly applicable while bottle 10c is held in an upright position, for example, for scrubbing of overhead shower areas.

Figure 6:
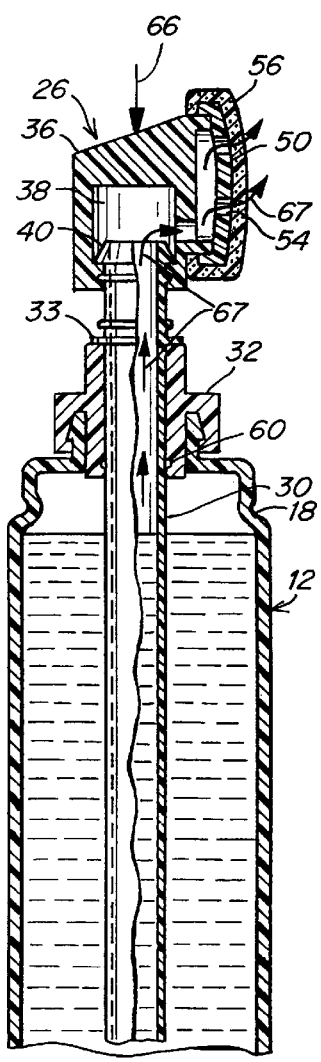
FIG. 6 is a longitudinal sectional view of the bottle of FIG. 5, showing the tube pushed back into the bottle.
Figure 7:
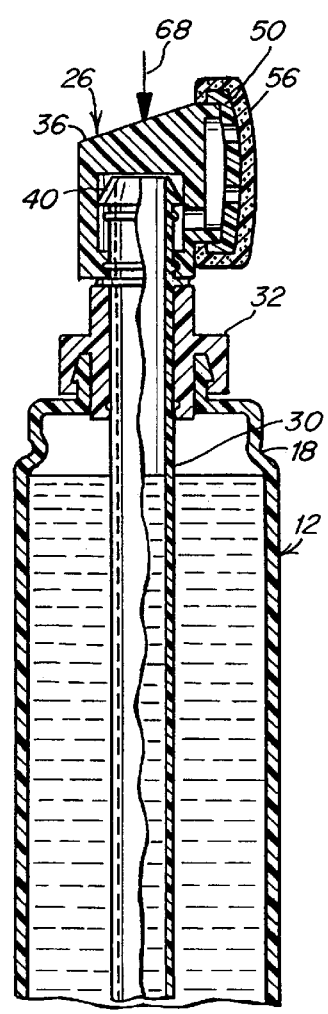
FIG. 7 is a longitudinal sectional view of the bottle of FIG. 6, showing the head fully pushed on the tube in the storage position, such that the valve therein prevents fluid flow to the applicator member.
Figure 20:
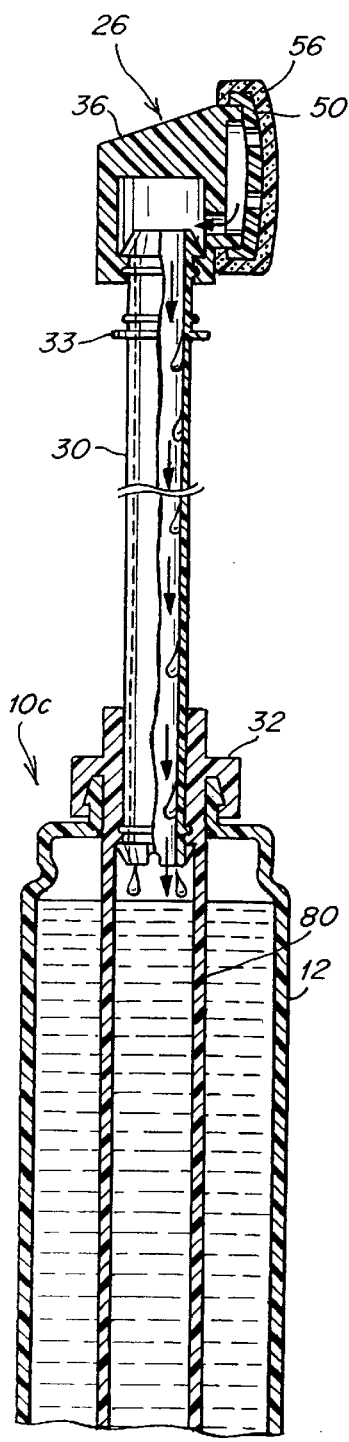
FIG. 20 is a longitudinal sectional view similar to FIG. 19, with the bottle placed upright to allow fluid to drain from the applicator head and tube back into the bottle.
Figure 21:
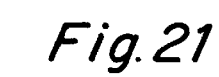
FIG. 21 is a longitudinal sectional view similar to FIG. 19, showing the tube pushed back into the bottle.
Figure 22:
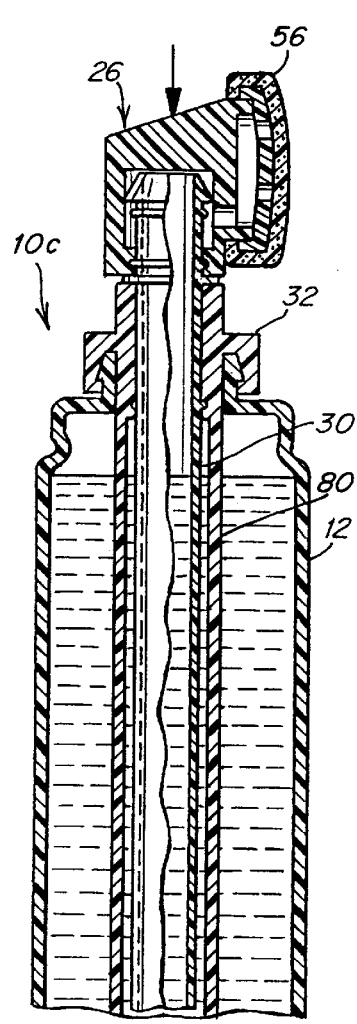
FIG. 22 is a longitudinal sectional view similar to FIG. 18, showing the head fully pushed on the tube in the storage position, such that the valve therein prevents fluid flow to the applicator member.

FIGS. 20–22 show the sequence of operations for returning bottle 10c to the stored position, and correspond to FIGS. 5–7 of bottle 10 according to the first embodiment.

Figure 23:
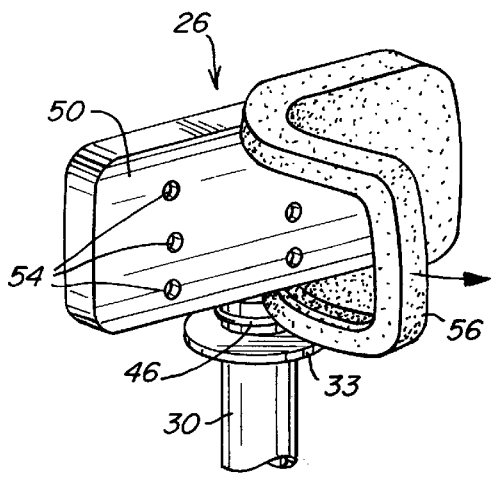
FIG. 23 is a front perspective view of the applicator head with the pad partially removed.
Figure 24:
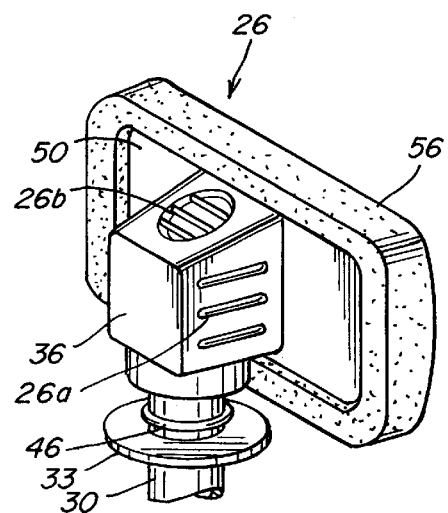
FIG. 24 is a rear perspective view of the applicator head.

Applicator head 26 is shown more particularly in FIGS. 23 and 24. As shown in FIG. 23, pad 56 is partially removed from manifold plate 50 of applicator head 26 in order to replace it with a new pad.

Referring now to FIGS. 25–28, an applicator head 126 according to a fifth embodiment of the present invention will now be described, in which elements corresponding to those in bottles 10, 10a and 10b according to the first through third embodiments are identified by the same reference numerals, and a detailed description of the common elements will be omitted for the sake of brevity.

As shown therein, applicator head 126 provides for direct dispensing as well as dispensing through pad 56. In this regard, opening 48 terminates in a nozzle 92 having a beveled or frusto-conical end. An annular bead 94 is provided around the circumference of nozzle 92.

A bracket 96 is hingedly secured to the upper end of body 36 of applicator head 126 by a hinge 98, which is preferably a living hinge. Bracket 96 includes a boss 99 having a through opening 100 for receiving and mating with nozzle 92. Boss 99 further includes an annular groove 101 on the internal surface thereof for receiving bead 94 in order to releasably secure bracket 96 in the closed position of FIGS. 25 and 27, thereby providing a snap fit seal. Plate 50 is secured to bracket 96 such that chamber 52 is defined between plate 50 and bracket 96. Bracket 96 further includes a finger gripping tab 102 for pivoting bracket 96 between the open position of FIGS. 26 and 28 and the closed position of FIGS. 25 and 27.

Figure 25:
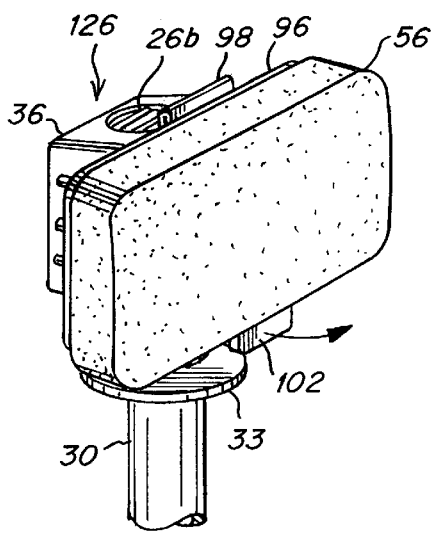
FIG. 25 is a front perspective view of the applicator head according to a fifth embodiment of the present invention, pivoted to a closed position.
Figure 26:
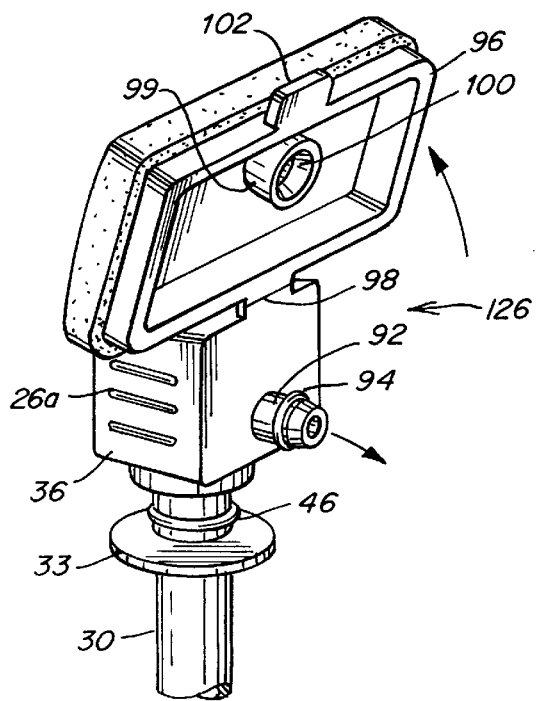
FIG. 26 is a front perspective view of the applicator head of FIG. 25, pivoted to an open position.
Figure 27:
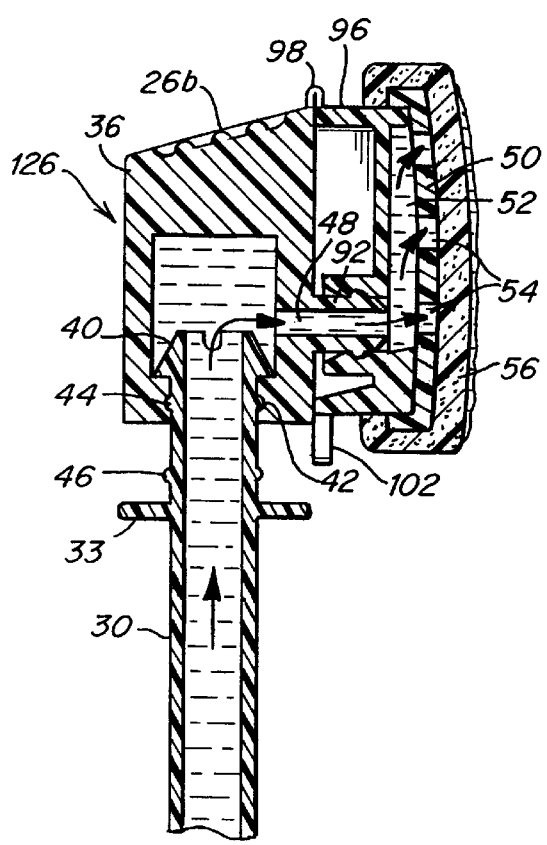
FIG. 27 is a longitudinal sectional view of the applicator head of FIG. 25.
Figure 28:
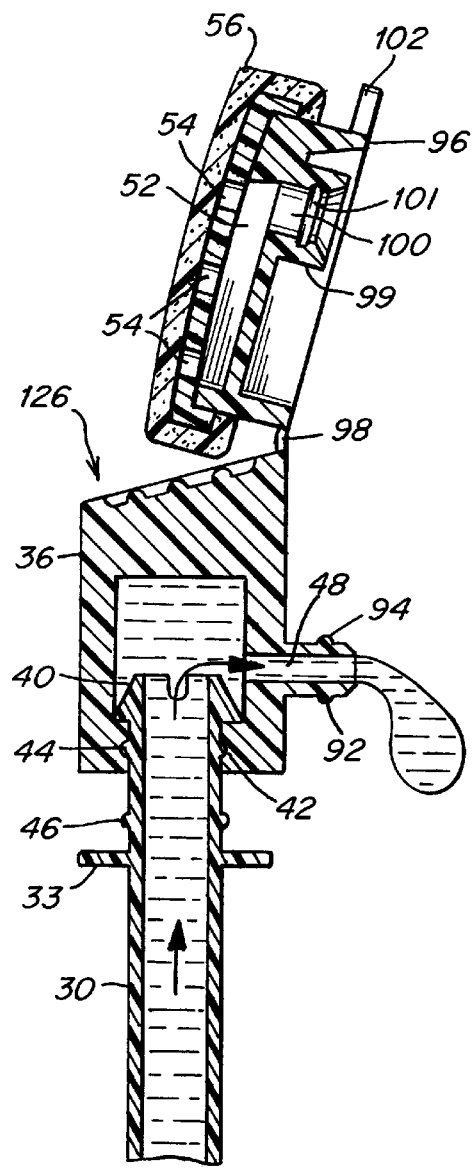
FIG. 28 is a longitudinal sectional view of the applicator head of FIG. 26.

With this embodiment, when bracket 96 is pivoted to the closed position of FIGS. 25 and 27, nozzle 92 extends through opening 100 of boss 99. In this position, fluid travels from tube 30, through nozzle 92, into chamber 52 and out openings 54 to pad 56. When bracket 96 is pivoted up to the open position of FIGS. 26 and 28, fluid is dispensed directly through nozzle 92 for direct dispensing. In such case, the bottle can be tipped at an angle of, for example, 45°, to dispense fluid into a user's hand. Further, due to the memory in the plastic of living hinge 98, bracket 96 and pad 56 are held out of the way in the open position.

The valve assembly in applicator head 126 is the same as in applicator head 26.

It will be appreciated that different applicator members 28 can be used with the present invention, other than the aforedescribed pad 56.

Figure 29:
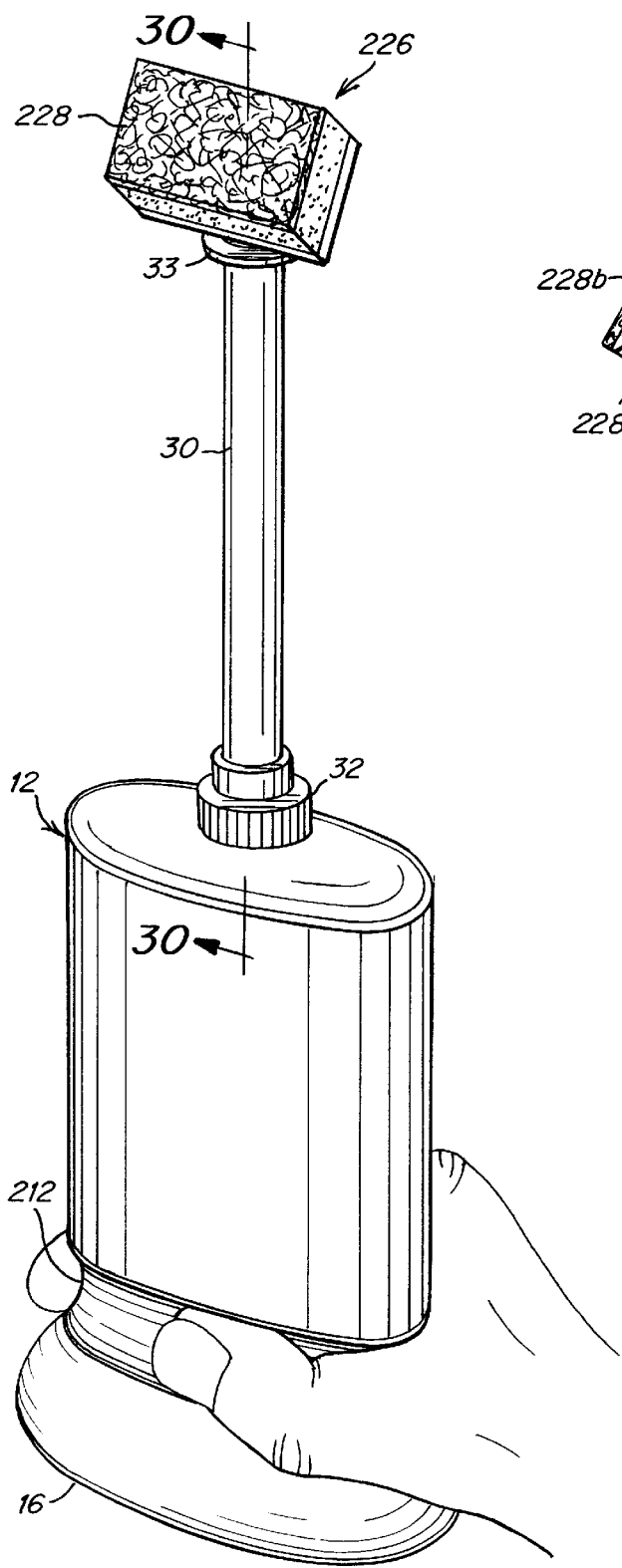
FIG. 29 is a perspective view of a bottle according to a sixth embodiment of the present invention, with a different applicator head and applicator member.
Figure 30:
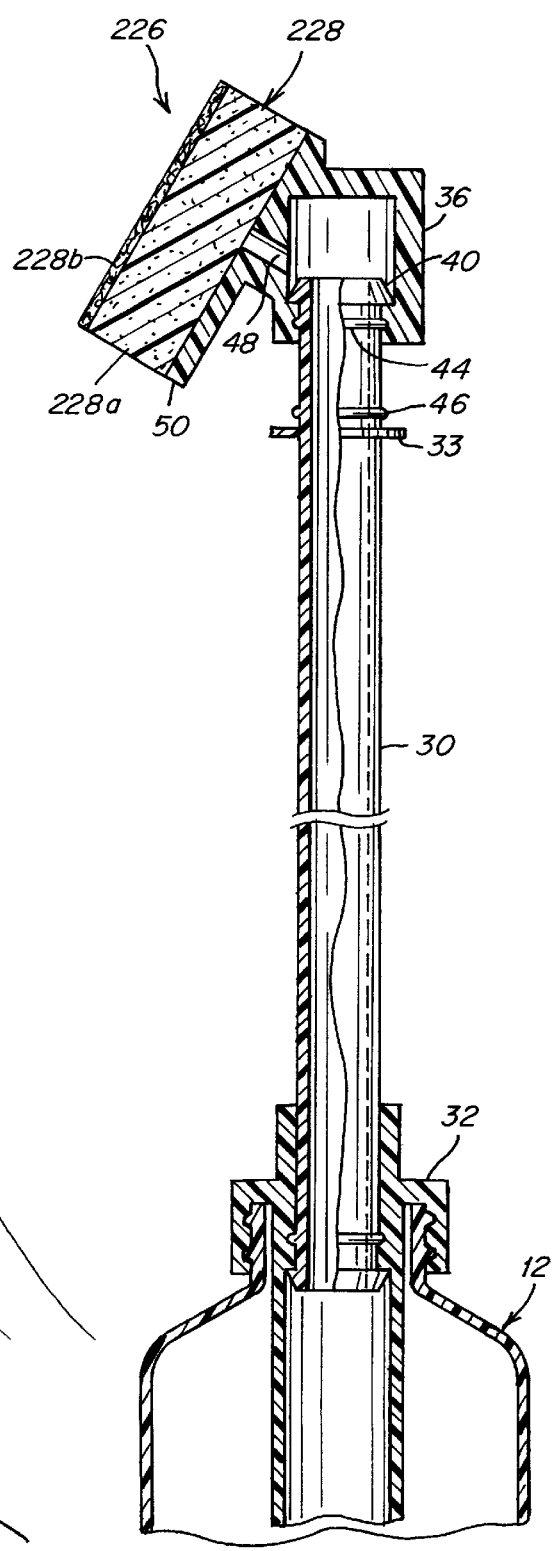
FIG. 30 is a sectional view taken along line 30—30 in FIG. 29.

Specifically, as shown in FIGS. 29 and 30, a bottle 10 according to a sixth embodiment of the present invention, is provided with a different applicator head 226 and applicator member 228. As shown therein, applicator member 228 is formed by an absorbent sponge or foam pad 228a having a stiffer and coarser front scrubbing surface 228b, for scrubbing tiles in a shower stall, etc. In such case, chamber 52 and openings 54 are eliminated, so that opening 48 terminates in plate 52 for impregnating foam head 228. It will be appreciated that dispensing opening 48 is positioned higher on pad 228a since a thinner liquid will tend to pool and drip from the bottom of pad 228a.

In addition, container 12 is shown with a circumferential indentation 212 to provide a better hand grip to facilitate scrubbing action, that is, back and forth motion without slipping. In such case, bottom 16 is provided with a wider base for stability.

Figure 31:
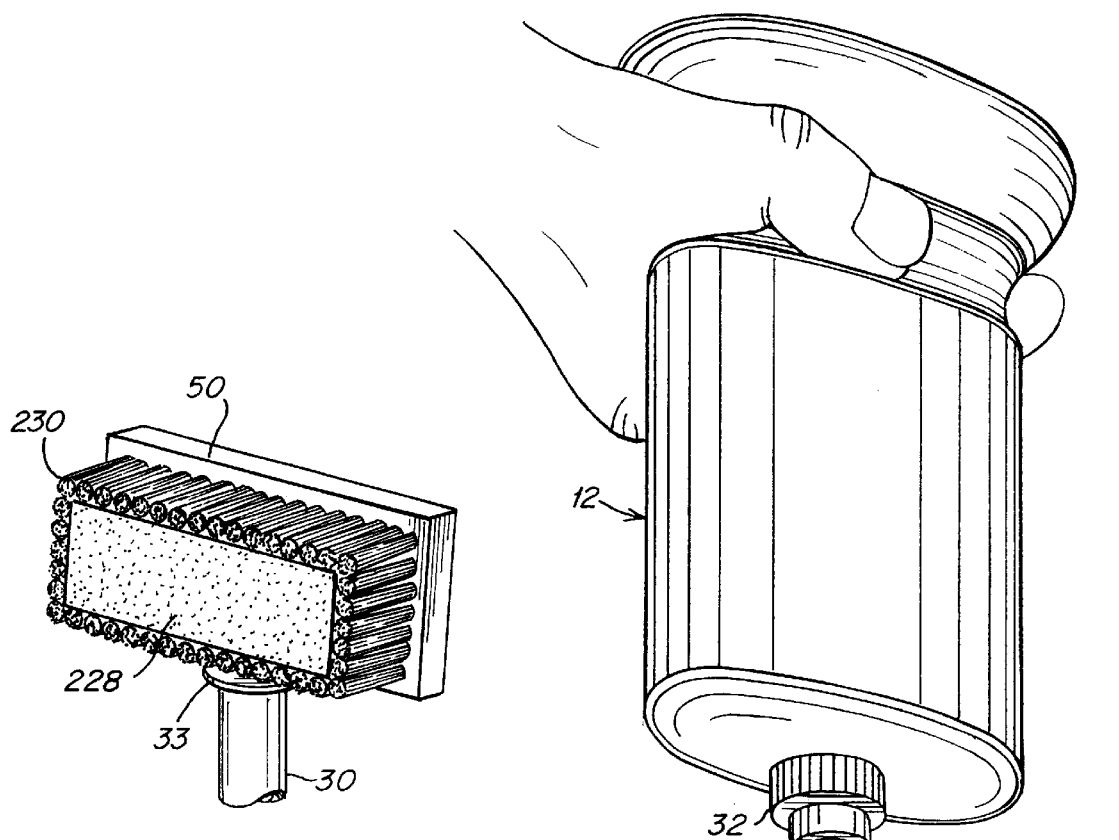
FIG. 31 is a perspective view of an applicator head and applicator member according to a seventh embodiment of the present invention.

FIG. 31 is a perspective view of an applicator head and applicator member according to a seventh embodiment of the present invention. As shown therein, brushes 230 are provided in surrounding relation to applicator member 228.

Figure 32:
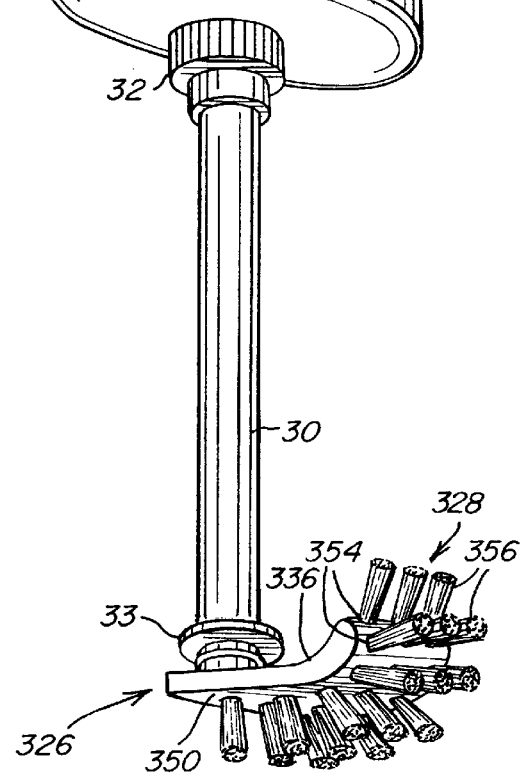
FIG. 32 is a perspective view of a bottle according to an eighth embodiment of the present invention, with a different applicator head and applicator member.

FIG. 32 is a perspective view of a bottle according to an eighth embodiment of the present invention, with a different applicator head 326 and applicator member 328.

In this embodiment, body 336 of applicator head 326 has an arcuate configuration, with plate 350 having a plurality of openings 354 therein. The applicator member 328 is formed by a plurality of brushes 356 secured to plate 350 at each opening 354, so that the fluid is dispensed through openings 354 onto brushes 356 for cleaning.

While the invention has been described above with respect to specific embodiments and implementations, it should be clear that various modifications can be made and that the features of the various embodiments can be interchanged and/or combined in any combination consistent with proper operation, within the scope of the invention as defined in the appended claims.

What is claimed is:

1. A combined applicator and bottle for storing a fluid and for applying the fluid, said bottle comprising:

a container having an opening;

an elongated tube having a longitudinal axis and an outer diameter, said tube being located in said opening, and said tube being slidable along said longitudinal axis relative to said container and being sealed against said container so that an intake end of the tube having an intake opening is located within the container and an outlet end of the tube having an outlet opening is located outside the container;

said tube having a duct extending at least partially in the direction of the longitudinal axis of the tube, said duct forming a fluid connection between said outlet opening of the tube and said intake opening that is situated within the container;

an applicator head mounted at the outlet end of the tube and having a dispensing opening and an applicator member for receiving the fluid from said outlet opening through said dispensing opening;

a valve assembly mounted in the applicator head for one of selectively (a) blocking flow of said fluid to said applicator member, and (b) permitting flow of said fluid to said applicator member, said valve assembly including:

a hollow area in said applicator head which slidably receives said outlet end of said tube therein, said hollow area having an inner diameter greater than the outer diameter of said tube and said dispensing opening has an axis which is at an angle to a sliding direction of said tube in said hollow area, and an annular flange at said outlet end of said tube and positioned within said hollow area, said annular flange having an outer diameter substantially equal to the inner diameter of said hollow area and which forms a seal with said walls of said applicator head in said hollow area; and a locking assembly which can releasably lock the outlet end of the tube in a first position in said hollow area such that said annular flange is positioned between said outlet opening and said dispensing opening to block flow of said fluid to said dispensing opening, and a second position in said hollow area in which said annular flange is not positioned between said outlet opening and said dispensing opening to permit flow of said fluid to said dispensing opening from said outlet opening.

2. The combined applicator and bottle according to claim 1, wherein said locking assembly includes an annular groove in an opening wall of said applicator head, a first bead on said tube which engages with said annular groove in said first position and a second bead on said tube which engages with said annular groove in said second position.

3. The combined applicator and bottle according to claim 2, wherein said axis of said dispensing opening is substantially transverse to the sliding direction of said tube in said hollow area.

4. The combined applicator and bottle according to claim 1, wherein said applicator head includes a main body having said hollow area, a manifold mounted to said main body, and an absorbent pad mounted on said manifold, said manifold being in fluid communication with said dispensing opening for dispensing fluid to said absorbent pad.

5. The combined applicator and bottle according to claim 4, wherein said absorbent pad and manifold are pivotally mounted to said main body such that the fluid can be dispensed through said manifold and absorbent pad when said manifold and absorbent pad are in a closed position, and can be dispensed directly through said dispensing opening when said manifold and absorbent pad are pivoted to an open position.

6. The combined applicator and bottle according to claim 5, wherein said main body further includes a nozzle in communication with said dispensing opening, and said manifold includes a boss having an opening for receiving said nozzle when said manifold and absorbent pad are pivoted to the closed position.

7. The combined applicator and bottle according to claim 1, wherein said intake end of said tube includes a bead therearound, and said container at said opening includes an annular groove for receiving said bead to releasably hold said tube in an extended position.

8. The combined applicator and bottle according to claim 1, further comprising a stop positioned around said tube near said outlet end thereof for limiting retraction of said tube into said container.

9. The combined applicator and bottle according to claim 1, wherein said container is made of a resilient and deformable material that permits squeezing thereof.

10. The combined applicator and bottle according to claim 1, wherein said applicator member is releasably mounted to said applicator head.

11. The combined applicator and bottle according to claim 1, wherein said applicator member comprises an absorbent pad.

12. The combined applicator and bottle according to claim 1, wherein said applicator member includes brushes mounted to said applicator head.

13. The combined applicator and bottle according to claim 1, wherein said axis of said dispensing opening is substantially transverse to the sliding direction of said tube in said hollow area.

14. The combined applicator and bottle according to claim 13, wherein said dispensing opening is formed in a wall of said applicator which defines said inner diameter of said hollow area.

15. The combined applicator and bottle according to claim 1, wherein said dispensing opening is formed in a wall of said applicator which defines said inner diameter of said hollow area.

16. A combined applicator and bottle for storing a fluid and for applying the fluid, said bottle comprising:

a container having an opening;

an elongated tube having a longitudinal axis and an outer diameter, said tube being located in said opening, and said tube being slidable along said longitudinal axis relative to said container and being sealed against said container so that an intake end of the tube having an intake opening is located within the container and an outlet end of the tube having an outlet opening is located outside the container;

said tube having a duct extending at least partially in the direction of the longitudinal axis of the tube, said duct forming a fluid connection between said outlet opening of the tube and said intake opening that is situated within the container;

an applicator head mounted at the outlet end of the tube and having an applicator member for receiving the fluid from said outlet opening;

a valve assembly mounted in the applicator head for one of selectively:
  (a) blocking flow of said fluid to said applicator member, and
  (b) permitting flow of said fluid to said applicator member; and a tube member in said container in surrounding and spaced relation to said tube and extending below said opening in said container into a liquid in said container, said tube member providing a path of travel of the fluid from said container to said tube when said tube is in an extended position out from said container.

17. The combined applicator and bottle according to claim 16, wherein said tube member includes a transverse extension along substantially the entire length thereof, said transverse extension including a longitudinal opening parallel to said tube, and said longitudinal opening is in fluid communication with the fluid in said container adjacent a top end of the container through a first transverse opening in said extension, and is in fluid communication with the tube adjacent a bottom of the container through a second transverse opening in said extension.

18. The combined applicator and bottle according to claim 17, wherein the fluid in said container is in fluid communication with said tube through said first transverse opening when said tube is in a fully extended position.

19. The combined applicator and bottle according to claim 16, wherein said tube is in fluid communication with the fluid in said container adjacent a top end of the container through a first transverse opening in said tube member and an annular space between said tube and said tube member when said container is turned upside down, and is in fluid communication with the fluid in said container adjacent a bottom of the container through a second transverse opening in said tube member when said container is upright.

20. The combined applicator and bottle according to claim 16, wherein:
said applicator head includes a dispensing opening; and
said valve assembly includes:
  a hollow area in said applicator head which slidably receives said outlet end of said tube therein; and
  said outlet end of said tube which forms a seal with walls of said applicator head in said hollow area for one of selectively:
    (a) blocking flow of said fluid to said dispensing opening, and
    (b) permitting flow of said fluid to said dispensing opening.

21. The combined applicator and bottle according to claim 20, wherein said outlet end of said tube includes an annular flange that forms a seal with said walls of said applicator head.

22. The combined applicator and bottle according to claim 20, further comprising a locking assembly which can releasably lock the outlet end of the tube in a first position in said hollow area to block flow of said fluid to said dispensing opening, and a second position in said hollow area to permit flow of said fluid to said dispensing opening.

23. The combined applicator and bottle according to claim 22, wherein said locking assembly includes an annular groove in an opening wall of said applicator head, a first bead on said tube which engages with said annular groove in said first position and a second bead on said tube which engages with said annular groove in said second position.

24. The combined applicator and bottle according to claim 20, wherein said dispensing opening has an axis which is substantially transverse to a sliding direction of said tube in said hollow area.

25. The combined applicator and bottle according to claim 20, wherein said applicator head includes a main body having said hollow area, a manifold mounted to said main body, and an absorbent pad mounted on said manifold, said manifold being in fluid communication with said dispensing opening for dispensing fluid to said absorbent pad.

26. The combined applicator and bottle according to claim 25, wherein said absorbent pad and manifold are pivotally mounted to said main body such that the fluid can be dispensed through said manifold and absorbent pad when said manifold and absorbent pad are in a closed position, and can be dispensed directly through said dispensing opening when said manifold and absorbent pad are pivoted to an open position.

27. The combined applicator and bottle according to claim 26, wherein said main body further includes a nozzle in communication with said dispensing opening, and said manifold includes a boss having an opening for receiving said nozzle when said manifold and absorbent pad are pivoted to the closed position.

28. The combined applicator and bottle according to claim 16, wherein said intake end of said tube includes a bead therearound, and said container at said opening includes an annular groove for receiving said bead to releasably hold said tube in an extended position.

29. The combined applicator and bottle according to claim 16, further comprising a stop positioned around said tube near said outlet end thereof for limiting retraction of said tube into said container.

30. The combined applicator and bottle according to claim 16, wherein said container is made of a resilient and deformable material that permits squeezing thereof.

31. The combined applicator and bottle according to claim 16, wherein said applicator member is releasably mounted to said applicator head.

32. The combined applicator and bottle according to claim 16, wherein said applicator member comprises an absorbent pad.

33. The combined applicator and bottle according to claim 16, wherein said applicator member includes brushes mounted to said applicator head.

* * * * *